(12) United States Patent
Kratzmeier

(10) Patent No.: US 6,835,773 B2
(45) Date of Patent: Dec. 28, 2004

(54) USE OF N-METHYLUREA FOR ELECTROPHORESIS OF SMALL PROTEINS

(75) Inventor: Martin Kratzmeier, Waldbronn (DE)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 10/411,072

(22) Filed: Apr. 10, 2003

(65) Prior Publication Data

US 2004/0204523 A1 Oct. 14, 2004

(51) Int. Cl.[7] .......................... C08J 23/00; B01D 57/02
(52) U.S. Cl. ..................... 524/813; 524/832; 524/845; 524/916
(58) Field of Search ................. 524/813, 832, 524/845, 916; 204/456, 469, 606

(56) References Cited

U.S. PATENT DOCUMENTS 2,783,276 A * 2/1957 Boatright et al. ........... 564/240
5,055,517 A * 10/1991 Shorr et al. ................. 524/813
6,042,710 A    3/2000 Dubrow ....................... 204/454

OTHER PUBLICATIONS

Poklar et al. "Thermodynamic stability of ribonuclease A in alkylurea solutions and preferential solvation changes accompanyin its thermal denaturation: A calorimetric and spectroscopic study", Protein Science, 8, 832–840(1999).*

Poklar, N. et al. "Thermodynamic Stability of Ribonuclease A in Alkylurea and Preferential Solvation Changes Accompanying its Thermal Denaturation:A Calorimetric and spectroscopic Study," 1999, The Protein Society, pp. 832–840.

* cited by examiner

*Primary Examiner*—Ling-Siu Choi

(57) ABSTRACT

A medium for use in electrophoresis comprising N-methylurea and a polyacrylamide gel. In particular, the medium is used in a system and method of electrophoretic separation comprising the introduction of a sample to the medium, and applying an electric field across the medium.

17 Claims, 4 Drawing Sheets

USE OF N-METHYLUREA FOR ELECTROPHORESIS OF SMALL PROTEINS

BACKGROUND OF THE INVENTION

1. Field of the Invention

The present invention relates to media for use in electrophoresis and a method of using such media. More particularly the present invention relates to a medium for use in electrophoresis having N-methylurea and a gel based on polyacrylamide and a method involving the introduction of a sample to a medium, and applying an electric field across the medium.

2. Description of the Prior Art

Electrophoresis is a technique used for the separation of DNA, RNA, proteins and other macro- and micro-molecular compounds. Biomolecules, such as proteins, amino acids, peptides, nucleotides, and nucleic acids are charged or can be made to be charged such that they will move in solution when subjected to an electrical field. The velocity at which the biomolecules migrate in this electrical field depends on the size, electrical charge, and other physical properties of the molecules.

The medium for this electrophoretic migration is typically a gel slab or a gel matrix within a capillary or a channel. These gels are often polymer networks formed by the mixture of a polymer with a certain amount of a cross-linker. The amount of cross-linker used determines the pore size within the gel through which the biomolecules migrate. U.S. Pat. No. 5,055,517 describes such a cross-linked polymer gel.

The biomolecular components separate across the electrophoretic medium over time when the electrical field is applied across the medium. One method of detecting and identifying the separated components involves staining the biomolecules with a dye and comparing the migration times to known standards. Another method of detection and identification involves measuring the fluorescence of the separated components.

When the molecules are to be separated by their size or molecular weights a denaturing agent is often added to the gel medium to improve resolution of the separated components. Urea can be used as this denaturing agent. However, the advantages in resolution obtained with the use of urea are offset by a negative effect on background fluorescence.

The effect of urea and alkylureas, such as N-methylurea, on the thermal stability, structural properties, and preferential salvation changes accompanying the thermal unfolding of ribonuclease A is described in "*Thermodynamic stability of ribonuclease A in alkylurea solutions and preferential salvation changes accompanying its thermal denaturation: A calorimetric and spectroscopic study,*" Protein Science 8:832–840 (1999). However, alkylureas have not previously been shown to improve the resolution of components separated by electrophoresis.

Accordingly, it would be desirable to provide a method, system, and a medium for electrophoresis that improves the resolution of components separated by electrophoresis while minimizing background fluorescence.

SUMMARY OF THE INVENTION

The present invention provides a medium for use in electrophoresis having N-methylurea and a gel capable of suspending the N-methylurea.

The present invention further provides an electrophoretic system having a medium and electrodes for introducing an electric field across the medium, wherein the medium has N-methylurea and a gel capable of suspending the N-methylurea.

The present invention further provides a method of electrophoretic separation involving the introduction of a sample volume to a medium, and applying an electric field across the medium, wherein the medium includes N-methylurea.

DETAILED DESCRIPTION OF THE INVENTION

Figure 1:
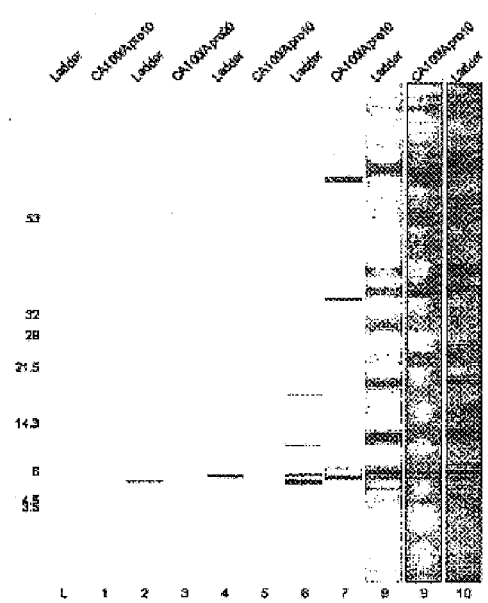
FIG. 1 shows gel-like images of separations using 2M urea and 0.5M N-methylurea in separate media for electrophoresis.
Figure 1:
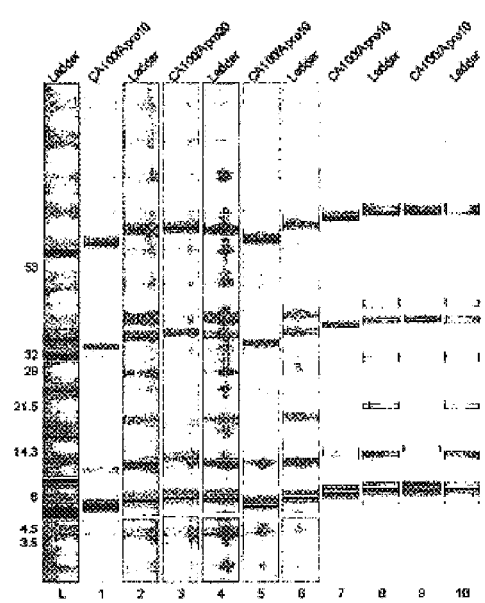

The present invention provides a medium for use in electrophoresis having N-methylurea and a gel capable of suspending the N-methylurea.

The present invention further provides an electrophoretic system having a medium and electrodes for applying an electric field across the medium, wherein the medium comprises N-methylurea and a gel capable of suspending the N-methylurea.

The present invention further provides a method of electrophoretic separation involving the introduction of a sample volume to a medium, and applying an electric field across the medium, wherein the medium includes N-methylurea.

The medium for use in electrophoresis and in the system and method of the present invention contains N-methylurea. The medium may also have a gel capable of suspending the N-methylurea. Examples of appropriate materials for inclusion in this gel include polyacrylamide, polydimethylacrylamide, polyethylene oxide, and polyvinylpyrrolidone. A preferred gel is a polydimethylacrylamide gel.

The N-methylurea is present in the medium in an amount effective to denature protein. A preferred concentration of N-methylurea in the medium is from between about 0.05 M to about 2 M. A most preferred concentration of N-methylurea in the medium is between about 0.1 M to about 0.5 M.

The resolution, or baseline separation of adjacent peaks, of sample components in electrophoresis depends on the characteristics of the proteins within a sample and can be limited by several factors that affect the migration behavior of the proteins within the medium used for electrophoresis. For example, protein heterogeneity that results in a larger peak or band width can reduce resolution. The use of N-methylurea in the medium of the present invention improved resolution over media having urea, particularly enhancing sizing resolution of proteins in the molecular weight range of about 5 to about 14 kDa. For purposes of this invention, resolution is stated as % resolution of overall molecular weight range. For example, using N-methylurea improves resolution in the molecular weight range of 5 to 50 kDa, and the resolution (i.e., baseline separation of adjacent peaks) is 10% between 10 and 50 kDa, and 1 kDa between 5 and 10 kDa. Without the use of N-methyl urea or urea (with its negative impact on background fluorescence) there is basically no separation of peaks and therefore no resolution below 10 kDa.

The medium for use in electrophoresis can be employed in various electrophoretic techniques. Non-limiting examples of electrophoretic techniques include SDS polyacrylamide electrophoresis (SDS-PAGE), capillary electrophoresis, and micro-channel/microfluidic channel electrophoresis.

A preferred type of electrophoresis to employ the medium is microfluidic-channel electrophoresis. An example of microfluidic-channel electrophoresis involves a micro-channel chip having a network of micro-channels that serve as paths for the migration of fluid sample volumes. A single sample volume or many sample volumes may be run on the same micro-channel chip simultaneously. The micro-channel chip is loaded into a device, such as a bioanalyzer for molecular assays, which provides a network of micro-electrodes onto the chip wells, thus supplying the necessary voltages and currents for the separation of the sample volume components. Micro-channel chip electrophoresis generally provides higher resolutions, smaller sample volume sizes, shorter analysis times, and reduced sample handling over traditional capillary electrophoresis. An example of this type of electrophoresis is described in U.S. Pat. No. 6,042,710, which is hereby incorporated herein by reference in its entirety.

The present invention further provides for an electrophoretic system having a medium and electrodes for applying an electric field across the medium. The medium comprises N-methylurea, as a denaturing agent, as well as a gel capable of suspending the N-methylurea. Examples of appropriate materials for inclusion in this gel include polyacrylamide, polydimethylacrylamide, polyethylene oxide, and polyvinylpyrrolidone. A preferred gel is a polydimethylacrylamide gel.

The N-methylurea is present in the medium in an amount effective to denature protein. A preferred concentration of N-methylurea in the medium is from between about 0.05 M to about 2 M. A most preferred concentration of N-methylurea in the medium is between about 0.1 M to about 0.5 M.

The electrophoretic system and its unique medium may be used in various electrophoretic techniques. Non-limiting examples of electrophoretic techniques include SDS polyacrylamide electrophoresis (SDS-PAGE), capillary electrophoresis, and micro-channel/microfluidic channel electrophoresis.

When used for microfluidic-channel electrophoresis, the electrophoretic system may also have a chip in which electrophoresis of samples takes place. Typically, the chip can have electrodes and a substrate which comprises a planar body structure in which grooves are fabricated to define capillary channels when overlaid with a cover element, also typically planar in structure. Exemplary substrates materials include, e.g., glass, quartz, silica, silicon, polymers, e.g., plastics like polydimethylsiloxanes (PDMS), polymethylmethacrylate (PMMA), polyurethane, polyvinylchloride (PVC), polystyrene, polysulfone, polycarbonate, polytetrafluoroethylene (Teflon™.), and a variety of others that are well known in the art. Substrates may take a variety of shapes or forms, including tubular substrates, e.g., polymer or fused silica capillaries, or the like. The medium is employed in the micro-channels formed in the substrate to bring about the separation of sample components passing through the micro-channels under the influence of an electric field induced across the medium by the electrodes.

The present invention also provides for a method of electrophoretic separation involving the introduction of a sample volume to a medium and applying an electric field across the medium. The medium comprises N-methylurea, as a denaturing agent, as well as a gel capable of suspending the N-methylurea. Examples of appropriate materials for inclusion in this gel include polyacrylamide, polydimethylacrylamide, polyethylene oxide, and polyvinylpyrrolidone. A preferred gel is a polydimethylacrylamide gel.

The N-methylurea is present in the medium in an amount effective to denature protein. A preferred concentration of N-methylurea In the medium is from between about 0.05 M to about 2 M. A most preferred concentration of N-methylurea in the medium is between about 0.1 M to about 0.5 M.

Typically, the medium is introduced into a capillary channel or micro-channel. This introduction may be as simple as placing one end of the channel into contact with the medium and allowing the medium to wick into the channel. Alternatively, vacuum or pressure may be used to drive the medium solution into the capillary channel. In integrated channel systems such as those used in chip electrophoresis, the medium is typically placed into contact with a terminus of a common micro-channel, e.g., a reservoir disposed at the end of a separation channel, and slight pressure is applied to force the polymer into all of the integrated channels.

A sample containing a species for which separation is desired, is placed in one end of the separation channel and a voltage gradient is applied along the length of the channel. As the sample components are electrokinetically transported down the length of the channel and through the medium disposed therein, those components are resolved. The separated components are then detected at a point along the length of the channel, typically near the terminus of the separation channel distal to the point at which the sample was introduced.

Detection of separated species is typically carried out using a fluorescent detection system that is well known in the art. Typically, such detection systems operate by detecting fluorescence of an associated labeling moiety. The labeling moiety is a fluorescent or fluorogenic-labeling group coupled to the various macromolecules or injected into the micro-channels with the medium. These labeling techniques are generally well known in the art, and include the use of covalently attached fluorescent labeling groups and associative labeling groups which preferentially associate with the macromolecular species of interest, or are only detectable, e.g., fluorescent or fluorogenic, when associated with the macromolecules of interest. Examples of such moieties include dyes of the Cy family (Amersham Pharmacia Biotech) and dyes of the Syto-, Alexa-, and TOTO families (Molecular Probes).

Typically, such systems utilize a light source capable of directing light energy at the separation channel as the separated species are transported past. The light source typically produces light of an appropriate wavelength to activate the labeling group. Fluorescent light from the labeling group is then collected by appropriate optics, e.g., an objective lens, located adjacent the capillary channel, and the collected light is directed at a photometric detector, such as a photodiode or photomultiplier tube. The detector is typically coupled to a computer, which receives the data from the detector and records that data for subsequent storage and analysis.

EXAMPLE 1

FIG. 1 shows gel-like images of separations using 2M urea and 0.5 N-methylurea. In this experiment, a protein size standard ("ladder") and a mixture of carbonic anhydrase (29 kDa) and aprotinin (6.5 kDa) in phosphate buffered saline (PBS) was applied alternately onto a protein electrophoresis glass chip. As a result, with the use of methylurea the baseline only increased by a factor of 2.7 which is still acceptable in terms of signal to noise ration, whereas with the use of urea the baseline increased by a factor of 5.1, leading to a decrease in sensitivity.

EXAMPLE 2

Figure 2:
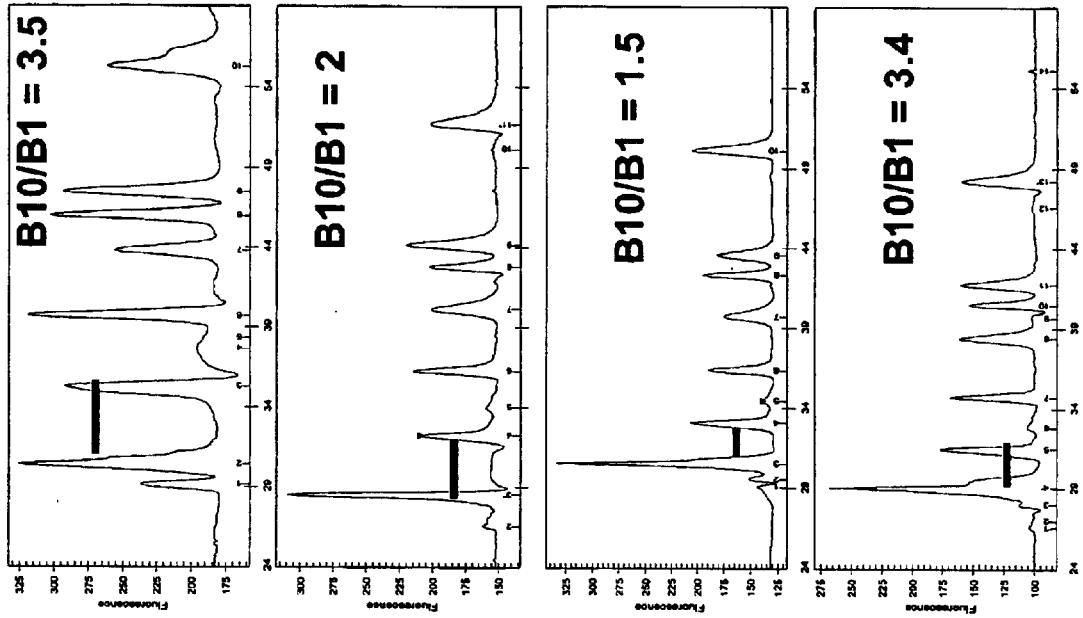
FIG. 2 shows electropherograms of separations using 2M N-methylurea, 1M N-methylurea, 0.5M N-methylurea, and 2 M urea in separate media for electrophoresis.

FIG. 2 shows electropherograms of separations using 2M N-methylurea, 1 M N-methylurea, 0.5M N-methylurea, and 2 M urea in separate media for electrophoresis. As seen on the figure, 0.5 M N-methylurea was about as effective in increasing the distance between the 6.5 kDa marker protein aprotinin and the system peak as 2M urea without the negative effect on baseline rise. Higher N-methylurea concentrations increased the resolution in that range even further but also showed a significant baseline rise over the time leading to decrease in sensitivity.

The use of N,N'-dimethyl urea and N-butyl urea were also found to increase the resolution over the use of urea. However, addition of even small amounts of these compounds increased viscosity of the gel matrix to such a degree as to cause serious problems in filling the micro-channel chip with the gel matrix. Additionally, the hydrophobicity of these compounds can be problematic. The N-methyl urea was found to have the positive effects on separation resolution without the degree of negative effect on gel viscosity shown by N,N'-dimethyl urea and N-butyl urea.

Figure 3:
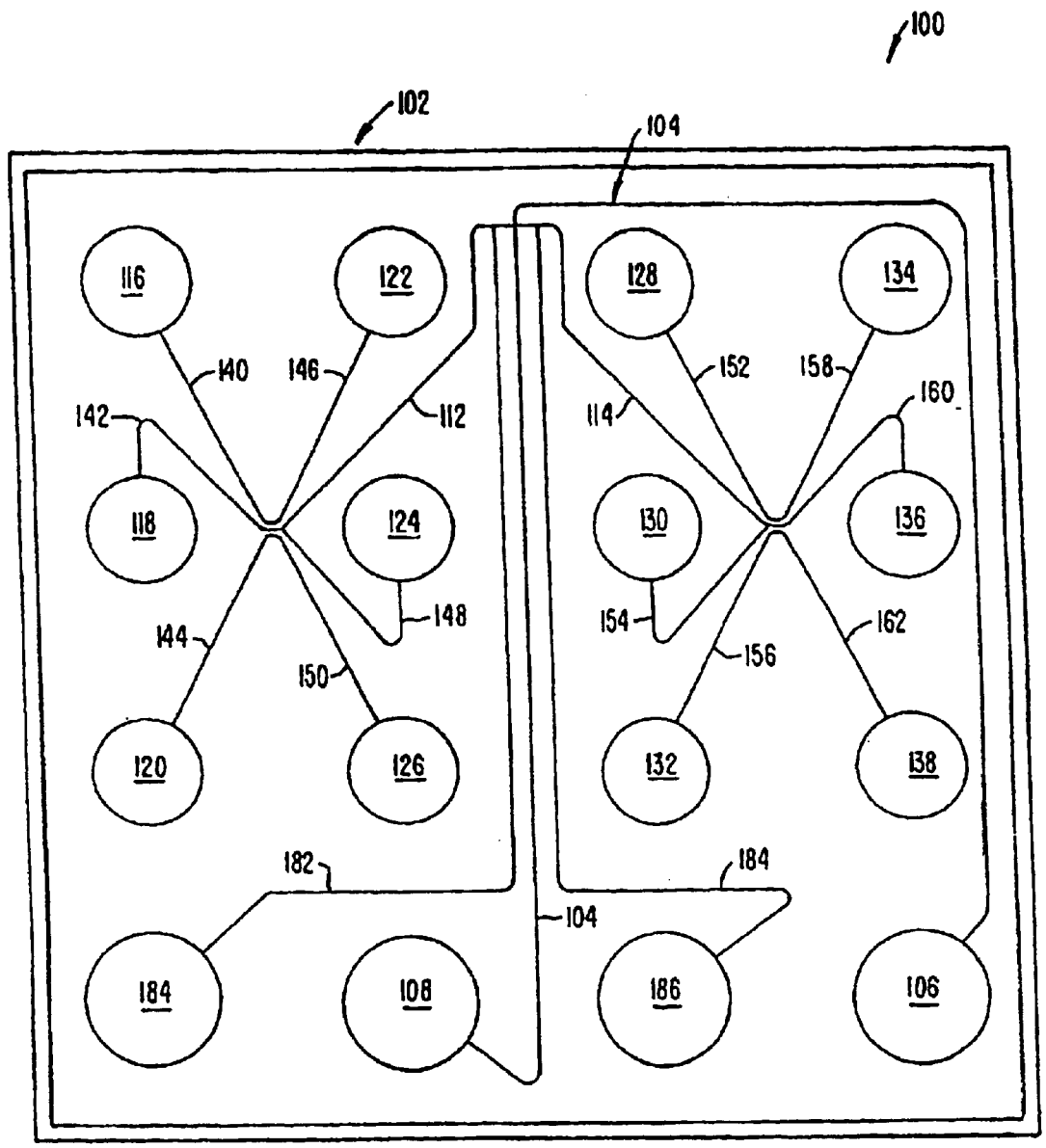
FIG. 3 is a schematic representation of micro-channel chip electrophoresis according to the present invention.

FIG. 3 shows a schematic representation of a typical micro-channel chip. In operation, sample materials are placed into one or more of the sample reservoirs 116–138. A first sample material, e.g., disposed in reservoir 116, is then loaded by electrokinetically transporting it through channels 140 and 112, and across the intersection with the separation channel 104, toward load/waste reservoir 186 through channel 184. Sample is then injected by directing electrokinetic flow from buffer reservoir 106 through analysis channel 104 to waste reservoir 108, while pulling back the sample in the loading channels 112:114 at the intersection. While the first sample is being separated in analysis channel 104, a second sample, e.g., that disposed in reservoir 118, is preloaded by electrokinetically transporting it into channels 142 and 112 and toward the load/waste reservoir 184 through channel 182. After separation of the first sample, the second sample is then loaded across the intersection with analysis channel 104 by transporting the material toward load/waste reservoir 186 through channel 184. Components of the sample are detected as they pass a point of detection at the terminal end of the separation channel 104. Components are preferably detected by their fluorescence. Data from the detection can be translated into gel-like images (bands) and electropherograms (peaks).

Figure 4:
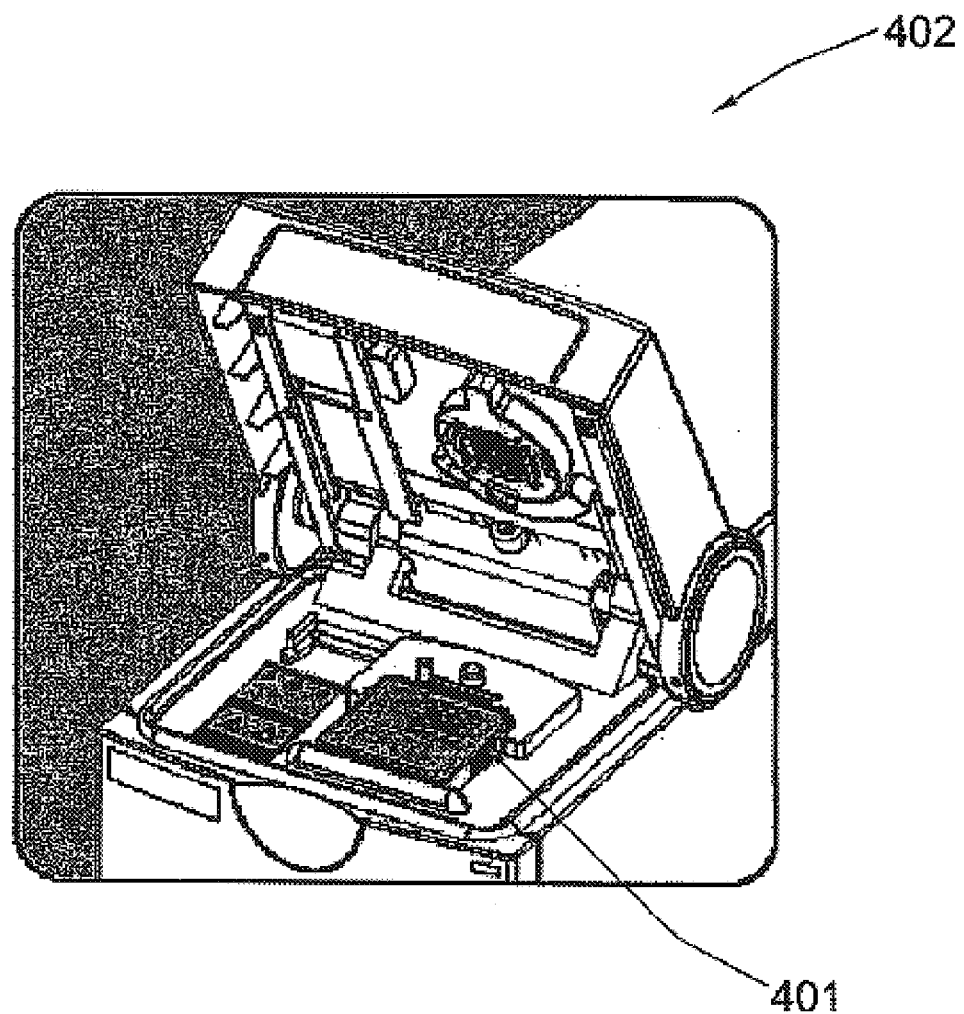
FIG. 4 is a schematic representation of the insertion of the micro-channel chip of FIG. 3 into a bioanalyzer for molecular assays.

FIG. 4 shows the insertion of a micro-channel chip (401) in a bioanalyzer for molecular assays (402).

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A medium for use in electrophoresis comprising:
   N-methylurea; and
   a gel which is capable of suspending said N-methylurea;
   wherein said gel is selected from the group consisting of: polyacrylamide, polydimethylacrylamide, polyethylene oxide, and polyvinyl pyrrolidone.

2. The medium of claim 1, wherein said N-methylurea is present in said medium in an amount effective to denature protein.

3. The medium of claim 1, wherein said N-methylurea is present in said medium in a concentration of between about 0.05 M to about 2 M.

4. The medium of claim 1, wherein said electrophoresis is selected from the group consisting of: SDS polyacrylamide electrophoresis (SDS-PAGE), capillary electrophoresis, and micro-channel/microfluidic channel electrophoresis.

5. The medium of claim 4, wherein said micro-channel is disposed within a chip.

6. The medium of claim 5, wherein said chip comprises a material selected from the group consisting of: glass, quartz, silica, silicon, and polymers.

7. An electrophoretic system comprising:
   a medium comprising N-methylurea and a gel capable of suspending said N-methylurea; and
   electrodes for applying an electric field across said medium;
   wherein said gel is selected from the group consisting of: polyacrylamide polydimethylacrylamide, polyethylene oxide, and polyvinyl pyrrolidone.

8. The electrophoretic system of claim 7, wherein said N-methylurea is present in said medium in an amount effective to denature protein.

9. The electrophoretic system of claim 7, wherein said N-methylurea is present in said medium in a concentration of between about 0.05 M to about 2 M.

10. The electrophoretic system of claim 7, wherein said electrophoretic system is selected from the group consisting of: SDS polyacrylamide electrophoresis (SDS-PAGE), capillary electrophoresis, and micro-channel/microfluidic channel electrophoresis.

11. The electrophoretic system of claim 10, wherein said micro-channel is disposed within a chip.

12. The electrophoretic system of claim 11, wherein said chip comprises a material selected from the group consisting of: glass, quartz, silica, silicon, and polymers.

13. A method of electrophoretic separation comprising:
   introducing a sample to a medium comprising N-methylurea and a gel capable of suspending said N-methylurea, wherein said gel is selected from the group consisting of: polyacrylamide, polydimethylacrylamide, polyethylene oxide, and polyvinyl pyrrolidone; and
   applying an electric field across said medium sufficient to cause separation of components of said sample.

14. The method of claim 13, wherein said N-methylurea is present in said medium in a concentration of between about 0.05 M to about 2 M.

15. The method of claim 13, wherein said electrophoretic separation is selected from the group consisting of: SDS polyacrylamide electrophoresis (SDS-PAGE), capillary electrophoresis, and micro-channel/microfluidic channel electrophoresis.

16. The method of claim 15, wherein said micro-channel is disposed within a chip.

17. The method of claim 16, wherein said chip comprises a material selected from the group consisting of: glass, quartz, silica, silicon, and polymers.

* * * * *